(12) United States Patent
Hoffman et al.

(10) Patent No.: US 7,679,063 B2
(45) Date of Patent: Mar. 16, 2010

(54) METHOD AND APPARATUS FOR IDENTIFYING PHOTOCATALYTIC COATINGS

(75) Inventors: Wayne Hoffman, Spring Green, WI (US); Wayne Knoble, Richland Center, WI (US)

(73) Assignee: Cardinal CG Company, Eden Prairie, MN (US)

( * ) Notice: Subject to any disclaimer, the term of this patent is extended or adjusted under 35 U.S.C. 154(b) by 276 days.

(21) Appl. No.: 11/557,281

(22) Filed: Nov. 7, 2006

(65) Prior Publication Data
US 2007/0109543 A1 May 17, 2007

Related U.S. Application Data

(60) Provisional application No. 60/734,241, filed on Nov. 7, 2005.

(51) Int. Cl.
*G01J 3/42* (2006.01)
(52) U.S. Cl. ...................................................... 250/375
(58) Field of Classification Search ................ 250/372, 250/375
See application file for complete search history.

(56) References Cited

U.S. PATENT DOCUMENTS

| | | | |
|---|---|---|---|
| 2,246,501 A | 6/1941 | Bradner | |
| 3,395,278 A * | 7/1968 | McDivitt | ................... 356/632 |
| 3,612,692 A | 10/1971 | Kruppa | |
| 3,636,917 A | 1/1972 | Baker | |
| 3,773,420 A | 11/1973 | Conroy | |
| 3,801,349 A | 4/1974 | Wilson | |
| 3,922,093 A | 11/1975 | Dandliker | |
| 4,072,426 A | 2/1978 | Horn | |
| 4,284,356 A | 8/1981 | Heilman | |
| 4,352,016 A | 9/1982 | Duffy | |
| 4,352,017 A | 9/1982 | Duffy | |
| 4,495,558 A * | 1/1985 | Cath et al. | ................... 205/791 |
| 4,511,800 A | 4/1985 | Harbeke | |
| 4,538,912 A | 9/1985 | Shaw | |
| 4,653,908 A | 3/1987 | Yajima | |
| 4,697,082 A | 9/1987 | Bartelsen | |
| 4,721,389 A | 1/1988 | Dejaiffe | |
| 4,815,856 A | 3/1989 | Bruce | |
| 4,831,264 A | 5/1989 | Fujiwara | |
| 4,841,156 A | 6/1989 | May | |
| 4,845,374 A | 7/1989 | White | |
| 4,966,455 A | 10/1990 | Avni | |
| 4,976,545 A | 12/1990 | Kipphan | |
| 5,146,097 A | 9/1992 | Fujiwara | |
| 5,162,660 A | 11/1992 | Popil | |

(Continued)

FOREIGN PATENT DOCUMENTS

WO     WO 2007053788 A1 * 5/2007

*Primary Examiner*—David P Porta
*Assistant Examiner*—David S Baker
(74) *Attorney, Agent, or Firm*—Fredrikson & Byron, P.A.

(57) ABSTRACT

A method of and apparatus for identifying the presence of thin photocatalytic (PCAT) coatings on glass surfaces. An apparatus is disclosed that can determine whether a PCAT coating (which may comprise titanium dioxide, for example) having a thickness of less than about 100 Å is present on the surface of a substrate such as glass. The apparatus may measure the reflectance of electromagnetic energy (such as light energy) at the surface of a substrate using energy at selected wavelengths or wavelength ranges. The apparatus may determine reflectance values for PCAT coated surfaces of any thickness, as well as for uncoated surfaces.

21 Claims, 12 Drawing Sheets

U.S. PATENT DOCUMENTS

| | | |
|---|---|---|
| 5,229,835 A | 7/1993 | Reinsch |
| 5,329,357 A | 7/1994 | Bernoux |
| 5,490,728 A | 2/1996 | Schietinger |
| 5,581,355 A * | 12/1996 | Myers et al. ................ 356/632 |
| 5,657,124 A | 8/1997 | Zhang |
| 5,717,216 A * | 2/1998 | McCoy et al. ................ 250/372 |
| 5,796,484 A | 8/1998 | Honma |
| 5,966,214 A | 10/1999 | Imbrock |
| 5,978,074 A | 11/1999 | Opsal |
| 6,088,104 A | 7/2000 | Peterson |
| 6,326,079 B1 | 12/2001 | Boire et al. |
| 6,413,581 B1 | 7/2002 | Greenberg et al. |
| 6,633,831 B2 | 10/2003 | Nikoonahad |
| 6,656,518 B2 | 12/2003 | Takahashi |
| 6,683,695 B1 * | 1/2004 | Simpson et al. ............. 356/632 |
| 6,734,967 B1 | 5/2004 | Piwonka-Corle |
| 6,784,431 B2 | 8/2004 | Shelley |
| 6,840,061 B1 | 1/2005 | Hurst et al. |
| 6,881,505 B2 * | 4/2005 | Tixhon ....................... 428/701 |
| 7,369,240 B1 * | 5/2008 | Abbott et al. ............... 356/429 |
| 2004/0032581 A1 | 2/2004 | Nikoonahad |

\* cited by examiner

*Prior Art*

METHOD AND APPARATUS FOR IDENTIFYING PHOTOCATALYTIC COATINGS

RELATED APPLICATION

This application is entitled to the benefit of provisional patent application No. 60/734,241 entitled "Method and Apparatus for Identifying Photocatalytic Coatings" filed Nov. 7, 2005, and incorporated herein by reference.

FIELD OF THE INVENTION

The invention relates generally to relatively thin photocatalytic coatings, and more particularly to a method and apparatus for identifying the presence of a relatively thin photocatalytic coating on a substrate.

BACKGROUND

A great deal of work has been done with the goal of developing self-cleaning coatings for windows and other substrates. One area of research has focused on photocatalytic coatings. Research in this area is founded on the ability of photocatalytic coatings to break down organic materials that come into contact with the coatings. One such photocatalyst appears to be titanium oxides (titanium dioxide, for example).

Windows may derive great benefit from photocatalytic coatings. For example, such windows may have self-cleaning characteristics. To the extent organic matter is deposited on such a window, the photoactive coating may act to oxidize the organic deposits, thereby having a cleaning effect on the surface of the window. To the extent residue survives this photocatalysis, such residue may be more easily removed by washing or, for outdoor window surfaces, by run-off rainwater.

Photocatalytic coatings have been developed which typically involve a titanium dioxide layer on a glass pane. The coatings are commonly provided with a relatively thick layer of titanium dioxide and/or a specific under-layer system designed for achieving high levels of photoactivity. Such photocatalytic coatings may be useful for absorbing ultraviolet radiation and photocatalytically degrading organic materials that may have collected on the coating. Thick titanium dioxide layers, unfortunately, produce high levels of visible reflectance, thus creating a somewhat mirror-like appearance. This high visible reflectance tends to exaggerate the appearance of dirt on a window.

Glass surfaces, such as windows, may have a photocatalytic (PCAT) coating applied in which the coating typically comprises a layer of titanium dioxide ($TiO_2$) that may be roughly 250 to 300 angstroms (Å) thick. PCAT coatings in this thickness range may be visible to the unaided human eye, and their presence may therefore be relatively easy to detect. Furthermore, at coating thicknesses in this range, visible light reflectance is significantly higher than it would be for the same substrate without the PCAT coating (typically in the range of 7 to 10% higher). Devices have been developed that can help distinguish between PCAT coated surfaces at these coating thicknesses and non-coated surfaces.

More recently, PCAT coatings have been developed in which the coating is significantly thinner than that described above. For example, work has been done to reduce the thickness of the $TiO_2$ layer in certain PCAT coated products to reduce and possibly eliminate reflectance and appearance differences between coated and non-coated surfaces, while maintaining the photocatalytic functionality of the coating.

The existence of thinner PCAT coatings may make it more difficult to distinguish between substrates coated with a "thin" PCAT coating and uncoated substrates. Visible differences between "thin" PCAT coatings and uncoated surfaces may be negligible. Furthermore, existing devices, which may have been designed for use with "thick" PCAT coatings (i.e., 250 to 300 Å), may not be able to distinguish surfaces with "thin" PCAT coatings from uncoated surfaces. These difficulties may pose additional challenges in the areas of manufacturing, quality assurance and distribution. For example, a customer or distributor receiving a shipment of the thin PCAT coated product may not be able to easily verify that they received the correct product due to the reduction in appearance and reflectance differences. New methods and devices for identifying the presence of "thin" PCAT coated products are therefore necessary.

SUMMARY OF THE INVENTION

Certain embodiments of the invention may include methods of identifying the presence or absence of a photocatalytic coating on a substrate. Further embodiments may include methods of identifying the presence or absence of a thin layer of a titanium-containing coating on a glass substrate.

Certain embodiments of the invention may include an apparatus for identifying the presence or absence of a thin layer of a titanium-containing coating on a glass substrate.

Certain embodiments of the invention may include a methods of measuring the thickness of a photocatalytic coating on a substrate. Certain further embodiments may include a method of measuring the thickness of a titanium-containing coating on a glass substrate.

Certain embodiments of the invention may include an apparatus for measuring the thickness of a titanium-containing coating on a glass substrate.

DETAILED DESCRIPTION

Figure 1:
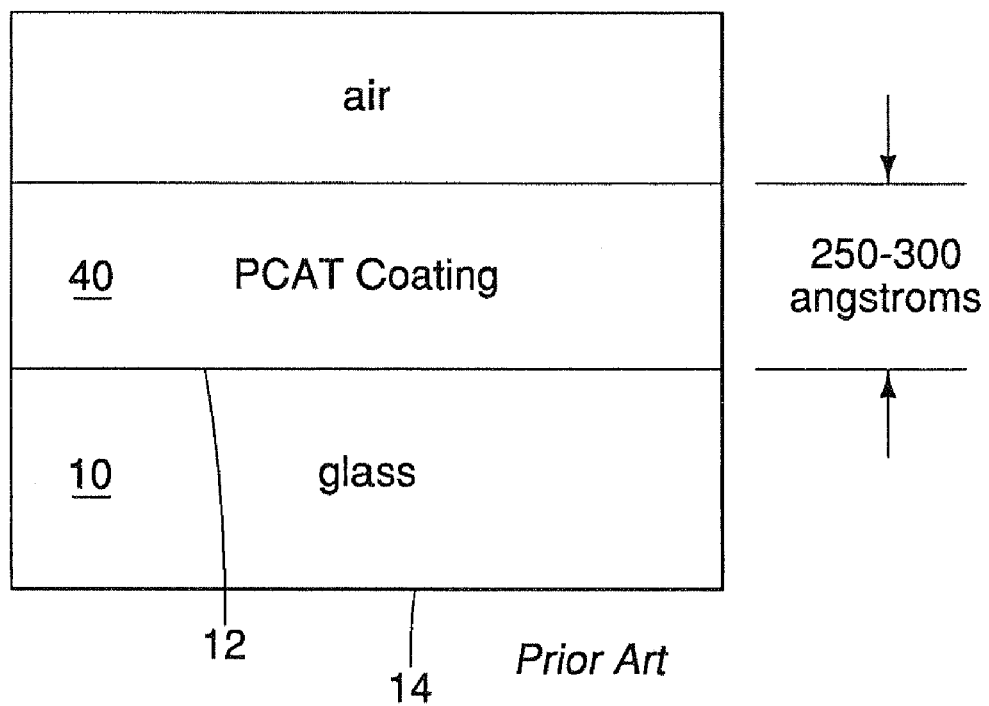
FIG. 1 is a schematic cross-sectional side view of a substrate bearing a photocatalytic (PCAT) coating.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

FIG. 1 is a cross-sectional side view of a substrate bearing a photocatalytic (PCAT) coating 40. As shown in FIG. 1, PCAT coatings with a thickness in the range of approximately 250-300 angstroms (Å) have been used to form a relatively low maintenance, self-cleaning surface on a substrate 10, such as glass. Such coatings may be useful for absorbing radiation (i.e., ultraviolet radiation) and photocatalytically degrading organic materials that may have collected on the coating surface. PCAT coatings in this thickness range may produce relatively high levels of visible reflectance, which can produce a mirror-like appearance and may exaggerate the appearance of dirt, for example. For reference purposes only, the PCAT coating 40 is hereinafter shown disposed on a "first" surface 12 of the substrate 10. A "second" surface 14 of the substrate 10 is also shown in FIG. 1.

A wide variety of substrate types may have a thin PCAT coating applied thereto. In some embodiments, the substrate 10 is a sheet-like substrate having generally opposed first 12 and second 14 major surfaces as shown in FIG. 1. For example, the substrate can be a sheet of transparent material (i.e., a transparent sheet). The substrate, however, is not required to be a sheet, nor is it required to be transparent. The substrate may, for example, be a polyester film, a polyethylene film, a terephthalate film, etc.

For many applications, the substrate will comprise a transparent (or at least translucent) material, such as glass or clear plastic. For example, the substrate may be a glass sheet (e.g., a window pane) in certain embodiments. A variety of known glass types can be used, and soda-lime glass will commonly be preferred. In certain preferred embodiments, the substrate is part of a window, skylight, door, or other glazing. In some cases, the substrate may form part of an automobile windshield, an automobile side window, an exterior or interior rear-view mirror, a bumper, a hubcap, a windshield wiper, or an automobile hood panel, side panel, trunk panel, or roof panel.

Substrates of various thicknesses can be used with the present invention. For example, the substrate may be a glass sheet having a thickness of about 1-6 mm. In one group of embodiments, the thickness of the substrate (which can be glass, plastic, or another material) may be between about 4 mm and about 20 mm. Thicknesses in this range, for example, may be useful for aquarium tanks (in which case, the substrate can optionally be glass or acrylic). When the substrate is float glass, it may have a thickness of between about 4 mm and about 19 mm. In another group of embodiments, the substrate may be a thin sheet (e.g., glass) having a thickness of between about 0.35 mm and about 1.9 mm. Embodiments of this nature can optionally involve the substrate being a sheet of display glass or the like. App. Ser. No. 60/659,491 describes the use of thin film coatings for glass sheets and other substrates and is hereby incorporated by reference in its entirety.

One application in which PCAT coatings have found utility is glass window coatings. For example, FIG. 2 is a partially broken-away perspective view of a window pane bearing a PCAT coating, the window pane being mounted in an exterior wall of a building.

Figure 2:
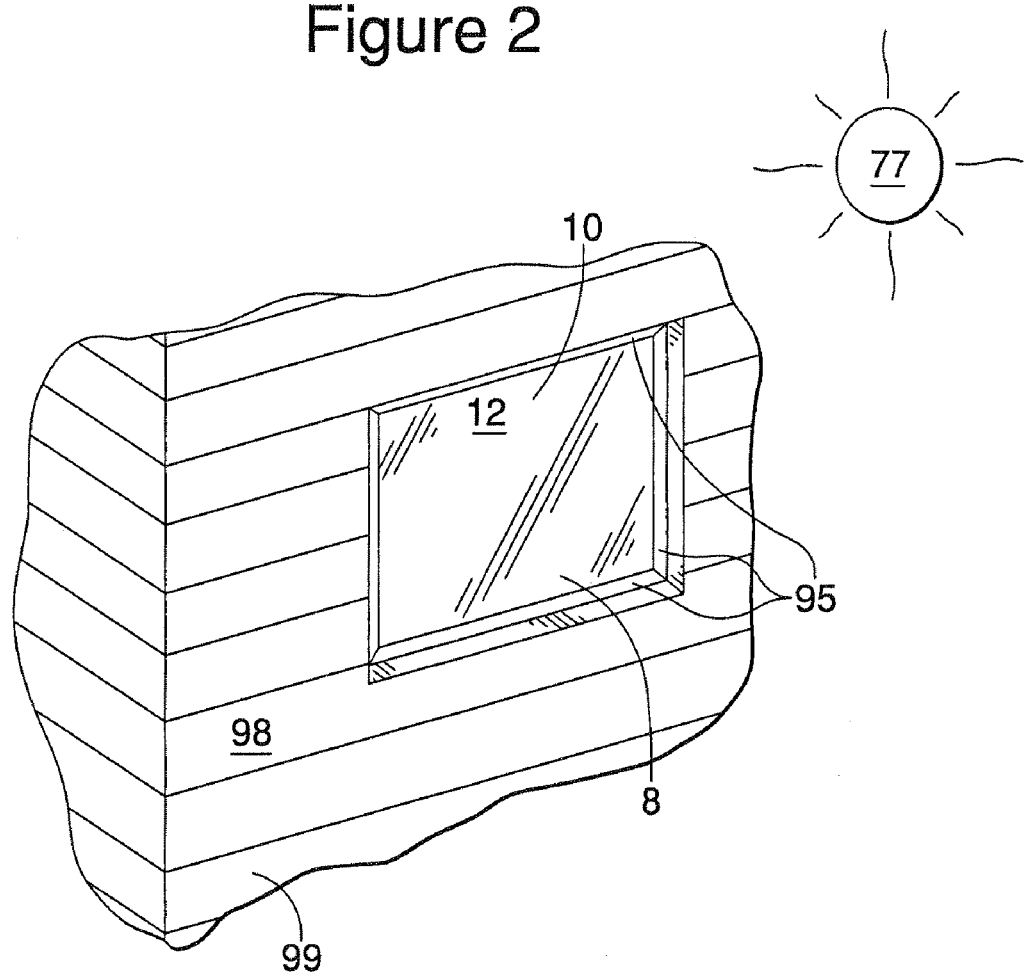
FIG. 2 is a partially broken-away perspective view of a window pane bearing a PCAT coating, the window pane mounted in an exterior wall of a building.

With reference to FIGS. 1 and 2, the PCAT coating 40 is typically disposed on the "first" surface 12 of a substrate 10. FIG. 2 exemplifies certain uses of PCAT coatings wherein the substrate 10 (which may be a glass pane) is a window pane that is mounted on a window frame 95 (e.g., an exterior wall 98 of a building 99). In certain applications, the coated first surface (i.e., surface 12) of such a window may be exposed to an outdoor environment such that the coating 40 may be in periodic contact with sun 77 and rain (not shown). In other applications, the PCAT coating may be applied to a an opposite surface 14 of a substrate 10 (see FIG. 1). In still other embodiments, the PCAT coating may be applied to both surfaces of a substrate 10. For insulating glass units (IGUs), the PCAT coating may also be applied to one or both inner surfaces of the IGU as well as one or both exterior surfaces.

Figure 3:
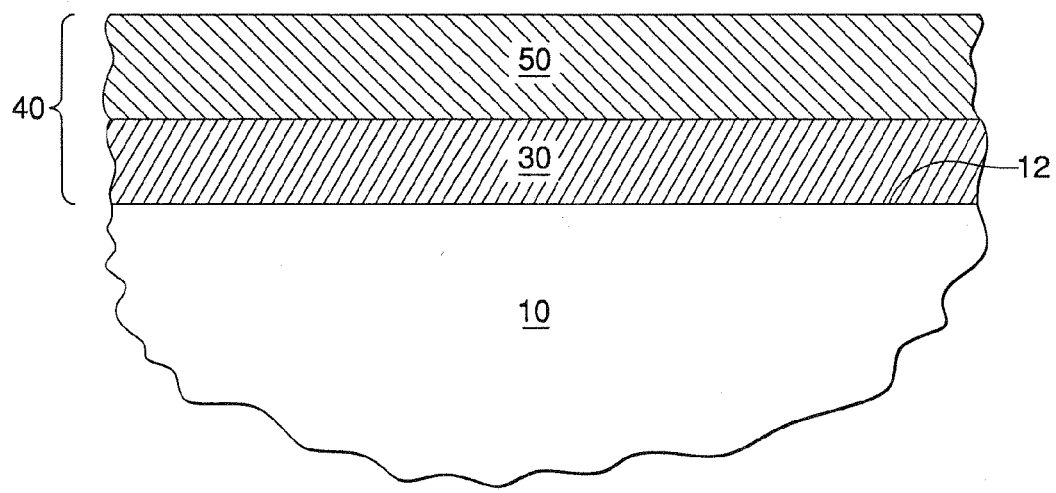
FIG. 3 is a partially broken-away schematic cross-sectional side view of a substrate bearing a PCAT coating.
Figure 4:
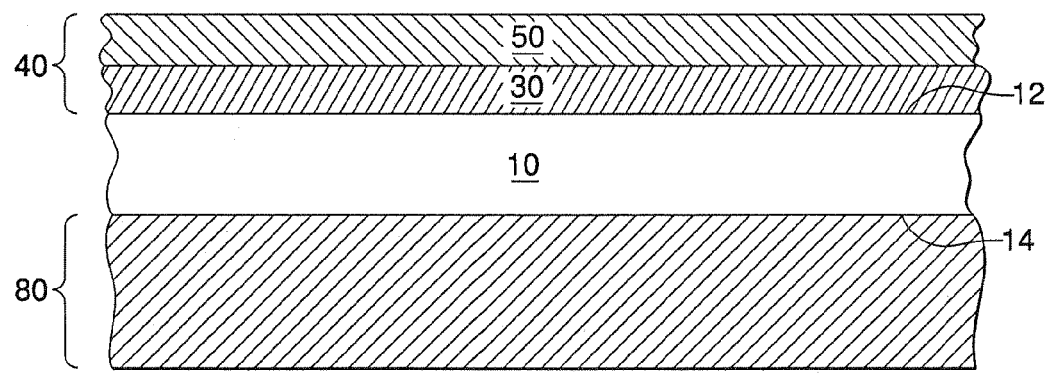
FIG. 4 is a partially broken-away schematic cross-sectional side view of a substrate bearing a PCAT coating and a low-emissivity (LOE) coating.

FIGS. 3 and 4 show partially broken-away schematic cross-sectional side views of substrates having a PCAT coating. The PCAT coating 40 is preferably deposited over (e.g., over an entirety of a first surface 12 of the substrate 10. In certain applications, the PCAT coating 40 may include two films: (1) a base film 30 deposited over a first surface 12 of the substrate 10; and (2) a titanium-containing film 50 deposited over the base film 30. The term "titanium-containing" is used herein to refer to a material that includes at least some titanium. Likewise, the term "silicon-containing" is used herein to refer to a material that includes at least some silicon. In FIG. 3, the base film 30 may comprise silica, for example, although this is not required. In certain embodiments, for example, the titanium-containing film 50 may be optionally deposited directly over the substrate 10 to form PCAT coating 40 (i.e., without a base film 30 present). There may be other types of PCAT coatings available. For example, zinc oxide could potentially be used. The embodiments of the invention are not limited to particular PCAT coatings but are intended to cover now known and future developed PCAT coatings.

In some embodiments, the base film 30 is deposited directly over the substrate 10 (e.g., directly over a first surface 12 of the substrate). The base film 30 generally comprises any dielectric film. In certain embodiments, film 30 may be comprised of silica (e.g., silicon dioxide). When the base film 30 is a silica film, it can include small amounts of an electrically-conductive material, such as aluminum, which may be oxidized in the film 30. For example, film 30 can be deposited by sputtering a silicon-containing target that includes a small amount of aluminum or another metal that enhances the electrical conductivity of the target. The base film 30 (an entire thickness of which may be comprised of silica) preferably has (e.g., is deposited at) a physical thickness of less than about 300 angstroms, and more preferably less than about 100 angstroms. In certain embodiments, the thickness of film 30 may be less than 95 angstroms.

The coating 40 may include a titanium-containing film 50 that may be deposited directly over the base film 30, or alternately may be deposited directly over the substrate 10. In certain embodiments, the titanium-containing film 50 may be deposited directly over an entirely or substantially amorphous base film 30. In some embodiments, the substrate 10 may be a glass sheet that has been subjected to a post-coating-deposition glass tempering procedure, and the base film 30 is entirely or substantially amorphous, such that the titanium-containing film 50 is deposited directly over an entirely or substantially amorphous base film.

The titanium-containing film 50 may comprise one or more other materials, such as oxides of iron, silver, copper, tungsten, aluminum, zinc, strontium, palladium, gold, platinum, nickel, cobalt, zirconium or combinations thereof. Preferably a major percentage (e.g., by weight) of the film 50 is comprised of titanium. In some embodiments, film 50 may consist essentially of titanium dioxide. In some embodiments, film 50 may consist essentially of substoichiometric titanium oxide (TiOx, where x is less than 2). The film 50 may have a thickness of less than about 100 angstroms. In certain embodiments, the film 50 may have a thickness of less than about 50 angstroms, preferably less than about 40 angstroms, and more preferably less than about 35 angstroms. In one particular embodiment, the film 50 has a thickness of between about 5 angstroms and about 30 angstroms.

FIG. 4 shows a partially broken-away schematic cross-sectional side view of a substrate 10 with a PCAT coating 40 disposed on a first surface 12 and a low-emissivity ("LoE") coating 80 disposed on a second surface 14. In certain embodiments of the invention, the existence of the LoE coating 80 on a second surface 14 of the substrate 10 will not affect the ability to analyze the PCAT coating 40 disposed on a first surface 12 of the substrate 10. The low-emissivity coating 80 is optional. When provided, any desired low-emissivity coating may be used. Suitable examples of low-emissivity coatings are described in U.S. patent application Ser. No. 09/728,435, entitled "Haze-Resistant Transparent Film Stacks," the entire teachings of which are incorporated herein by reference.

Figure 5:
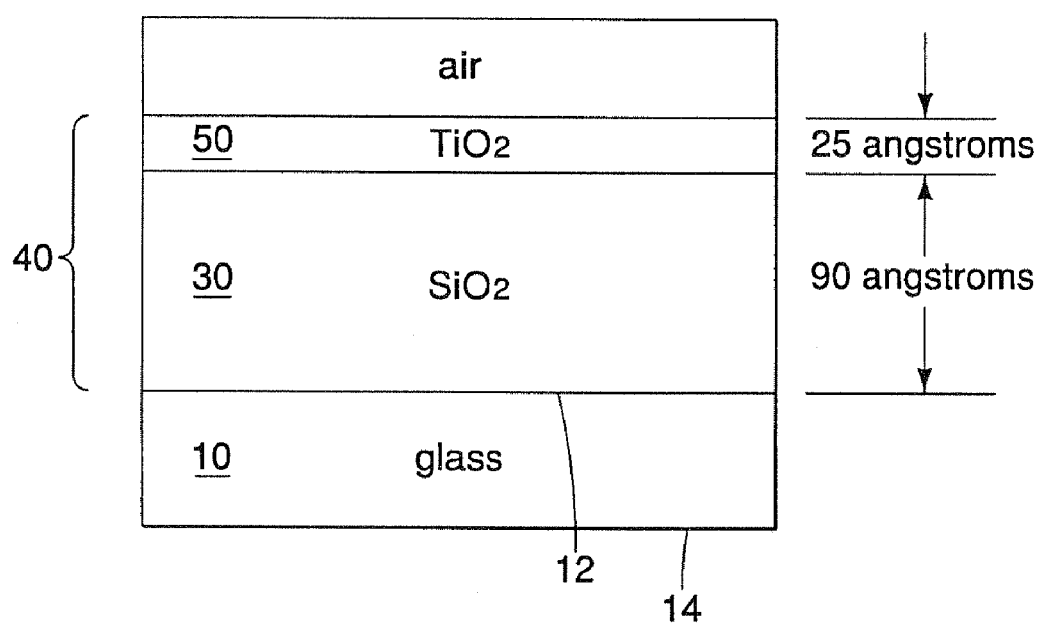
FIG. 5 is a schematic cross-sectional side view showing an example of a glass substrate having a photocatalytic (PCAT) coating whose presence may be detected by certain embodiments of the invention.

FIG. 5 is a cross-sectional side view showing exemplary characteristics and dimensions of one example of a relatively "thin" photocatalytic (PCAT) coating on a substrate. In FIG. 5, substrate 10 is made of glass, and the "thin" PCAT coating 40 is formed of two layers: base layer 30, comprised of silicon dioxide ($SiO_2$), and titanium-containing layer 50, comprised of titanium dioxide ($TiO_2$). Base layer 30 in the illustrated example has a thickness of about 90 angstroms (Å), while the titanium-containing layer 50 has a thickness of about 25 Å. The total thickness of the "thin" PCAT coating 40 is therefore about 115 Å according to this particular embodiment. Thus, the "thin" PCAT coating shown in FIG. 5 is significantly thinner than PCAT coatings in the range of 250-300 Å. The dimensions provided above are exemplary only, and only serve to show the relative difference in thickness presented by the newer "thin" PCAT coatings. A "thin" PCAT coating may comprise layers 30 and 50 that may be somewhat thinner or thicker than the dimensions shown in FIG. 5. Further, a "thin" PCAT coating may comprise a titanium-containing layer 50 disposed directly on a first surface 12 of substrate 10 (i.e., without an intervening base layer 30).

Applicants initially discovered that reflectance measurements across a range of wavelengths from about 300 nm to about 2500 nm revealed that the "thin" PCAT coated surface reflectance was different from the reflectance of non-coated surfaces in a range of about 300 nm to about 320 nm. Subsequent analysis below about 300 nm also revealed measurable differences between surface reflectance for thin PCAT coatings and that for uncoated substrates.

Figure 6:
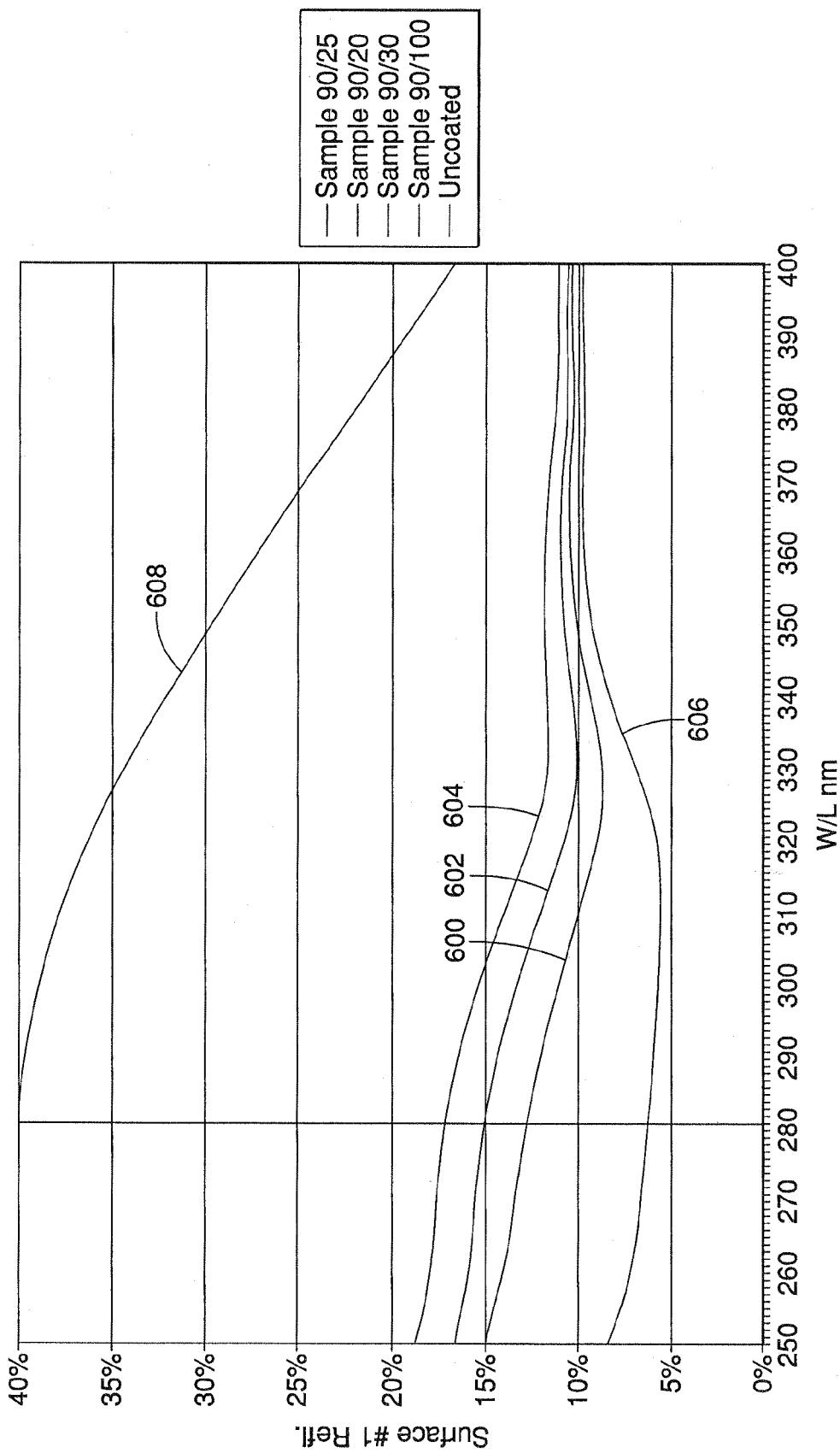
FIG. 6 is a reflectance curve showing percent reflectance of visible energy as a function of wavelength for various surfaces, including "thin" PCAT coated surfaces in accordance with an embodiment of the invention.

FIG. 6 is a chart of reflectance curves showing percent reflectance of light energy as a function of wavelength for various surfaces, including "thin" PCAT coated surfaces, "regular" (non-thin) PCAT coated surfaces, and uncoated glass. As shown in FIG. 6, PCAT coated surfaces (including both "thin" and "regular" PCAT varieties) exhibit reflectance curves at lower wavelengths (from about 250 nm to about 340 nm) that are measurably different from the reflectance curve for uncoated glass in this same range of wavelengths. However, at wavelengths above a certain value, the percent reflectance for certain PCAT coatings very nearly matches the percent reflectance for uncoated glass. For example, graphs 600, 602 and 604 represent coated samples that correspond to "thin" PCAT coatings having thicknesses of less than about 100 Å These "thin" PCAT coatings have percent reflectance values that are nearly indistinguishable from reflectance values for uncoated glass represented by graph 606 at wavelengths above about 350 nm. Thus, available methods used to distinguish between "regular" PCAT coatings and uncoated glass (for example, by using measured reflectance at higher wavelengths) may not function to distinguish "thin" PCAT coatings from uncoated glass. However, at wavelengths below approximately 320 nm, the difference in percent reflectance between "thin" PCAT coatings and uncoated glass may be enough to distinguish between the two. Graph 600 represents a coating on a substrate of first 90 Angstrom of $SiO_2$ followed by 20 Angstrom of $TiO_2$; Graph 602 represents a coating on a substrate of first 90 Angstrom of $SiO_2$ followed by 25 Angstrom of $TiO_2$; Graph 604 represents a coating on a substrate of first 90 Angstrom of $SiO_2$ followed by 30 Angstrom of $TiO_2$; and Graph 608 represents a coating on a substrate of first 90 Angstrom of $SiO_2$ followed by 100 Angstrom of $TiO_2$.

As shown in FIG. 6, the percent reflectance for uncoated glass at wavelengths below approximately 320 nm is less than about six percent, according to the sample results shown in FIG. 6. By contrast, the percent reflectance values for the "thin" PCAT coatings (labeled graphs 600, 602 and 604) are greater than about ten percent in this range of wavelengths. This difference in percent reflectance values over certain wavelength ranges enables one to distinguish the "thin" PCAT coatings from uncoated glass. Further, wavelengths below approximately 320 nm may be useful to distinguish both "thin" and "regular" PCAT coatings from uncoated glass due to the differences in measured percent reflectance in this wavelength range. A useful aspect of glass substrates worth noting is that glass completely absorbs light energy at wavelengths below about 330 nm, such that the effects of the reflectance of a coating on the surface opposite the PCAT surface (such as a low emissivity coating on the second surface 14, as shown in FIG. 4) are minimized or eliminated, and should therefore not interfere with the determination of whether a PCAT coating is present on a first surface. Thus, a method of determining whether a PCAT coating is present on the surface of a glass substrate should be unaffected by the presence or absence of a coating (such as a low emissivity coating, for example) on the opposite surface of the glass substrate when using wavelengths below about 330 nm.

Figure 7:
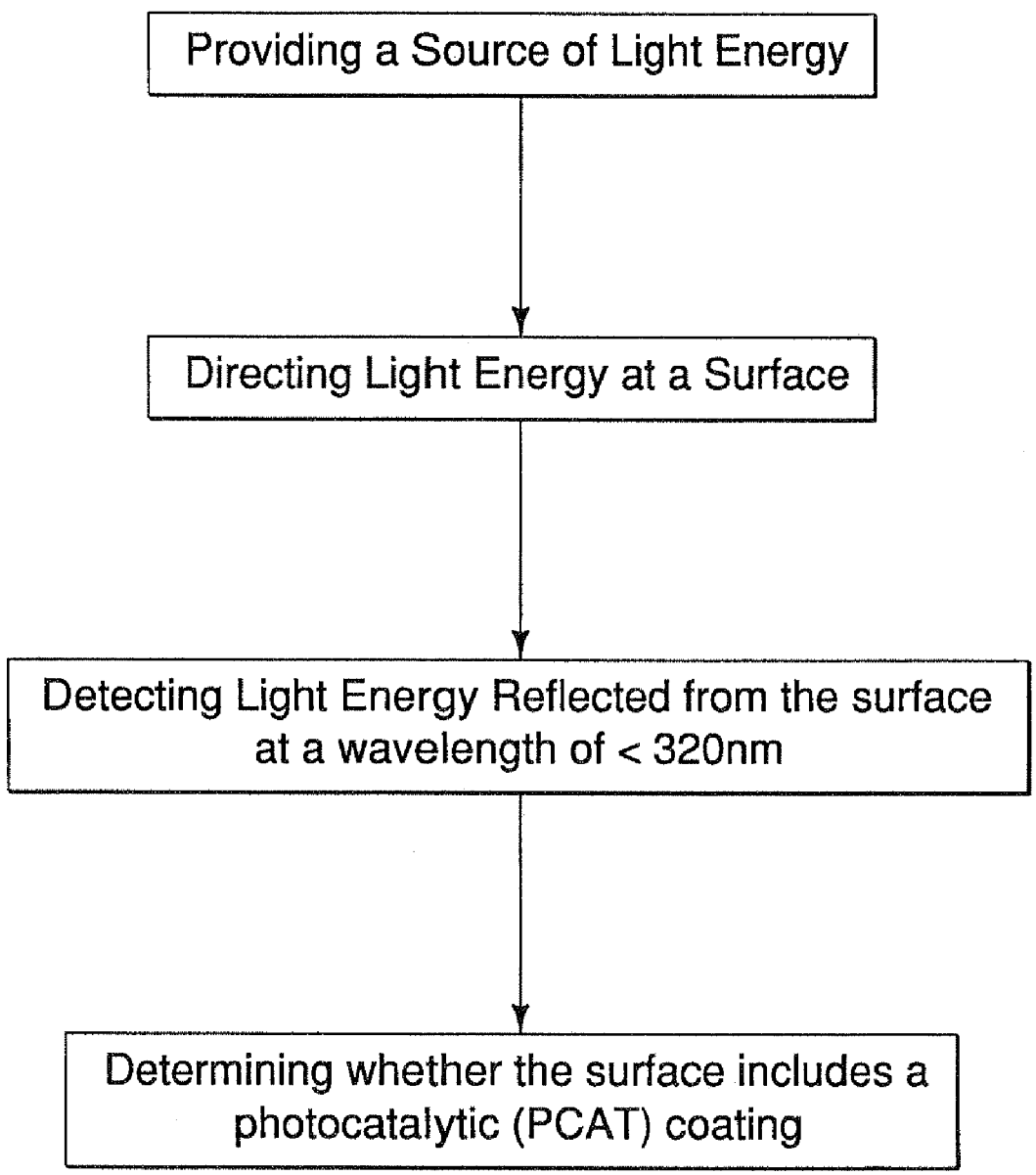
FIG. 7 is a block diagram of a method of identifying the presence of a PCAT coating on a surface in accordance with certain embodiments of the invention.

FIG. 7 is a block diagram of a method of identifying the presence of a PCAT coating on a surface in accordance with certain embodiments of the invention. Methods and devices in accordance with embodiments of the invention may identify the presence of both "thin" and "regular" (thick) PCAT coatings. Reference to PCAT coatings hereinafter includes both "thin" and "regular" PCAT coating thicknesses, unless specified otherwise. The first step in identifying the presence of a PCAT coating may include providing a source of light energy, for example. The light energy may comprise any available means of producing light energy that includes energy having wavelengths below approximately 320 nm, for example. According to certain embodiments of the invention, a laser source which produces a beam of laser energy at a specific wavelength (or relatively narrow range of wavelengths) may comprise the source of light energy. Such a laser source would preferably produce laser energy at wavelengths below approximately 320 nm. In one exemplary embodiment of the invention, the laser source may produce a narrow beam of laser energy centered on a wavelength of approximately 280 nm. In other embodiments of the invention, the source of light energy may comprise an ultraviolet lamp that produces ultraviolet light energy including energy at wavelengths below approximately 320 nm. In certain embodiments of the invention, an ultraviolet lamp may comprise a xenon or deuterium lamp capable of producing light energy including energy having wavelengths below approximately 320 nm. In a preferred embodiment, an LED emitting a wavelength of about 280 nm is used. Alternately, any electromagnetic source that produces energy below approximately 320 nm may be used.

A next step in a method of identifying the presence of a PCAT coating on a surface may include directing light energy at the surface. In some embodiments of the invention, the light energy may be directed at the surface at any suitable angle for measuring reflectance (from 0 to 90 degrees relative to the surface). The angle at which the incident light energy intersects a plane formed by the surface is referred to as the "angle of incidence," and is defined as the angle formed by a ray incident on a surface and a perpendicular to the surface at the point of incidence. For example, light energy that is perpendicular to the surface has an angle of incidence of 0 degrees. In certain embodiments of the invention, the light energy may be directed at the surface at an angle of incidence that is less than about 75 degrees, and preferably less than about 45 degrees, and more preferably less than about 30 degrees. The exact angle of incidence at which light energy may be directed to the surface may be a matter of design choice, reflecting a potential trade-off between the desire for a small device with the need to accommodate a light source, a detector, and any lenses or filters that may be needed to direct and receive light energy to and from the surface.

A next step in a method of identifying the presence of a PCAT coating may include detecting light energy reflected from the surface, wherein the detected light energy includes light energy having wavelengths less than approximately 320 nm. Reflected light energy may be detected using a suitable detector, such as a photodiode or a spectrophotometer.

A next step may include determining whether the surface includes a PCAT coating by comparing the reflected light energy detected by the detector to a known or reference value. In one embodiment, for example, the determination of whether a PCAT coating is present or not may be based upon a calculation of percent reflectance, which compares the reflected light energy at specified wavelengths to the incident light energy at the same specified wavelengths, for example. Alternately, the amount of incident light energy directed at the surface may be a relatively fixed or known quantity such that the reflected light energy detected by the detector may be directly compared to a reference or known value to determine whether the surface includes a PCAT coating.

Figure 8:
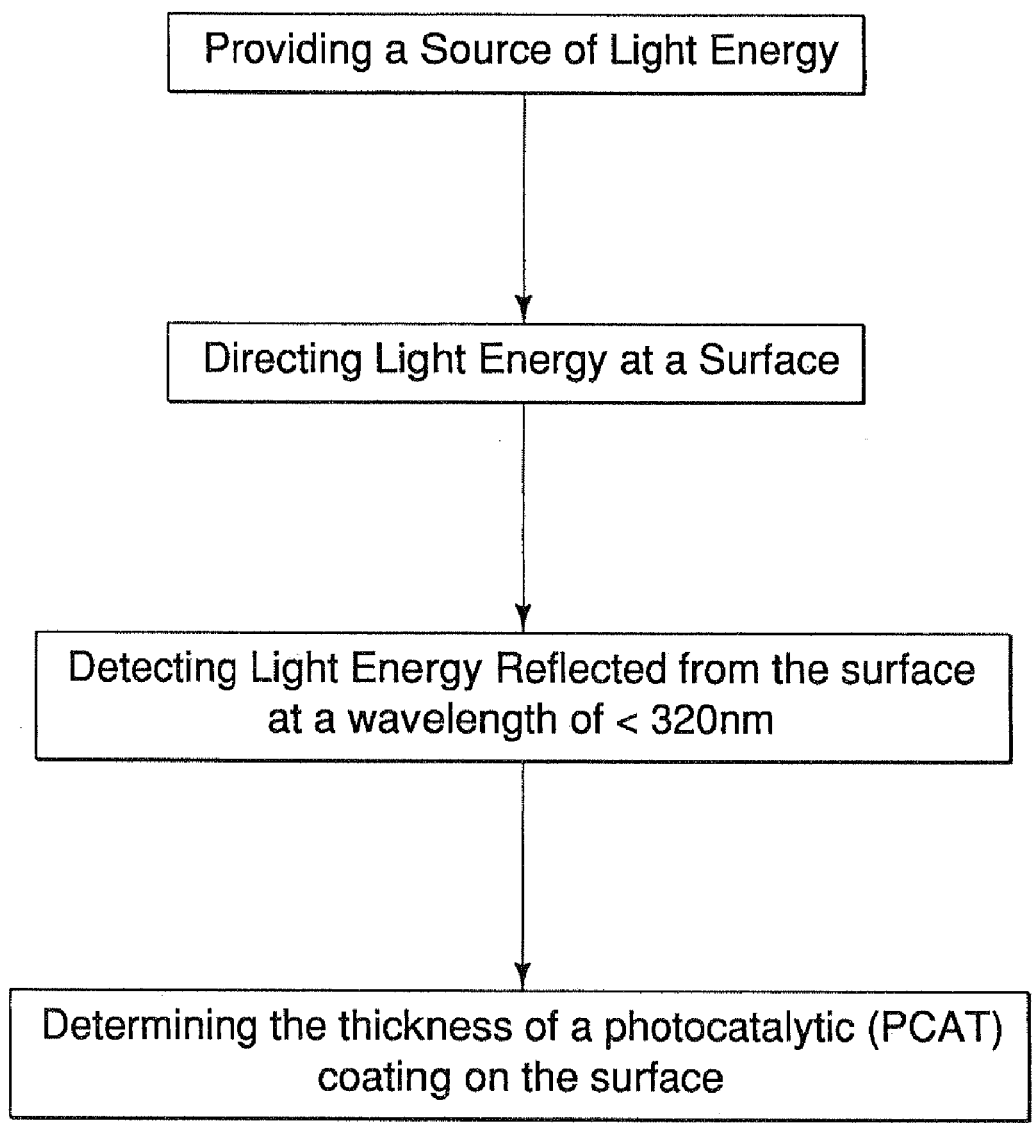
FIG. 8 is a block diagram of a method of measuring the thickness of a PCAT coating on a surface in accordance with certain embodiments of the invention.

FIG. 8 is a block diagram of a method of measuring the thickness of a PCAT coating on a surface in accordance with certain embodiments of the invention. The first several steps involved in measuring the thickness of a PCAT coating are similar to the above-described method of identifying the presence of a PCAT coating. The final step, namely that of determining the thickness of the PCAT coating, may involve the use of a look-up table to match the reflected light energy and/or percent reflectance values to historical or saved data corresponding to PCAT coatings of known thicknesses. Other methods of determining the thickness of a PCAT coating may be employed using such available measured parameters as incident light energy, reflected light energy, angle of incidence, angle of reflection, wavelength of light energy, bandwidth of light energy (range of wavelengths, for example), etc.

Figure 9:
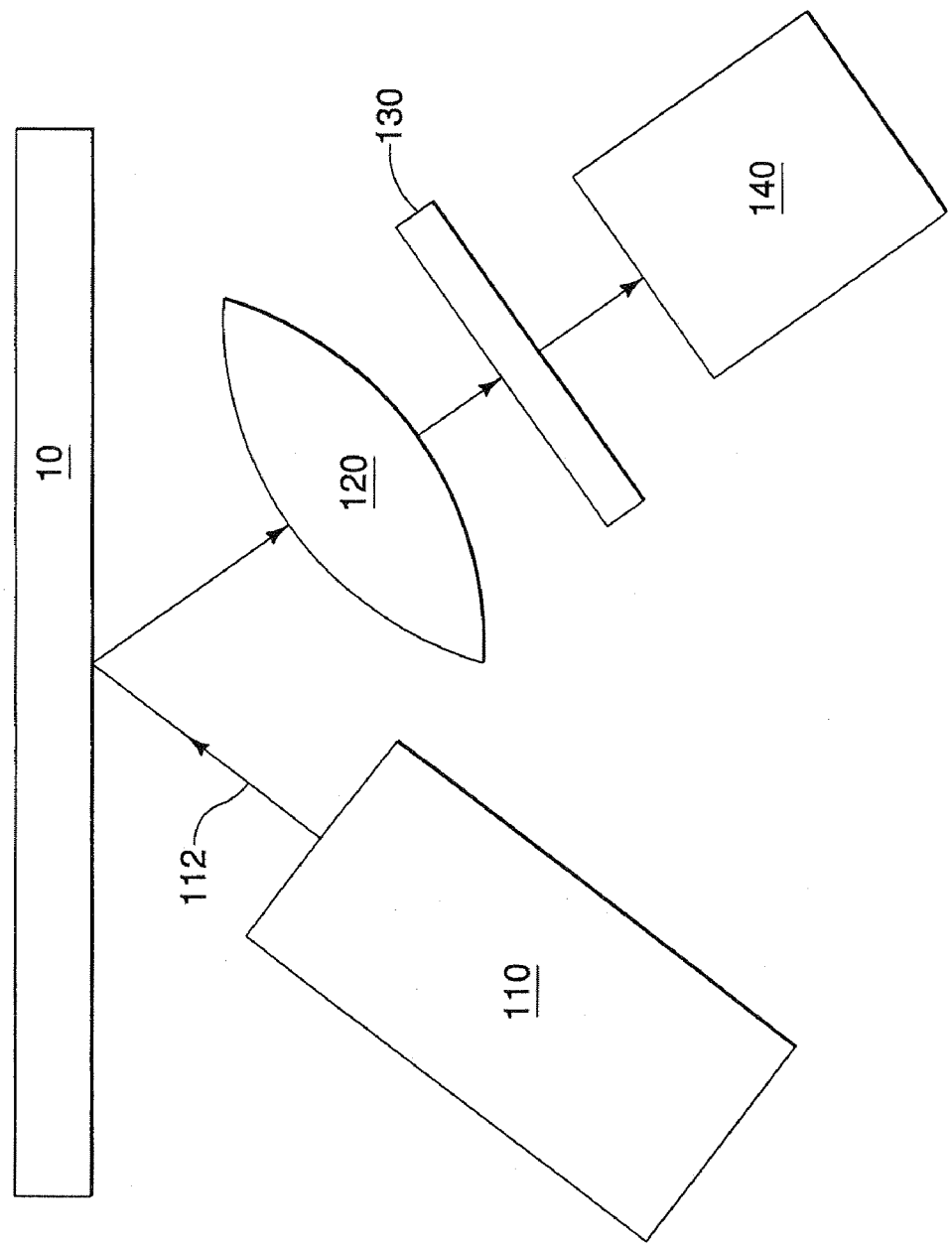
FIG. 9 is a schematic diagram of a device for analyzing a PCAT coating on a surface in accordance with certain embodiments of the invention.

FIG. 9 is a schematic diagram of a device for analyzing a PCAT coating on a surface in accordance with certain embodiments of the invention. FIG. 9 shows a substrate 10 which is to be analyzed for the presence of a photocatalytic coating. According to the embodiment shown in FIG. 9, a laser source 110 may be disposed relative to the substrate 10, the laser source being capable of producing a constant power, narrow beam, laser energy signal and directing it toward a surface of substrate 10. The laser energy signal 112 may have a wavelength of less than about 320 nm, and preferably less than about 300 nm. In one particular embodiment, for example, the laser energy signal 112 is a narrow beam laser energy signal. Preferably, a narrow beam would have a wavelength ranging from about 250 to about 320 nm. Also shown in FIG. 9 are lens 120 and filter 130, for receiving the reflected light energy and directing it toward the photodiode 140. The lens 120 may be a fused silica lens, for example. The photodiode 140 may be a broad area photodiode which, when used in conjunction with lens 120, may prevent angle and distance changes between the glass and the detector from changing the amount of reflected light received by the photodiode 140. Filter 130 may be an ultraviolet (UV) short pass filter. Filter 130 may be employed to block visible light from reaching photodiode 140. For example, filter 130 may be adapted to pass light energy signals within a narrow range of wavelengths, and may significantly attenuate signals outside the given narrow range of wavelengths. For example, in an embodiment where light energy signal 112 is centered at 266 nm, for example, filter 130 may be adapted to attenuate signals having wavelengths below about 261 nm and above about 271 nm, for example. Alternately, filter 130 may be adapted to attenuate signals having wavelengths above a certain wavelength (i.e., above about 271 nm, for example).

Figure 10:
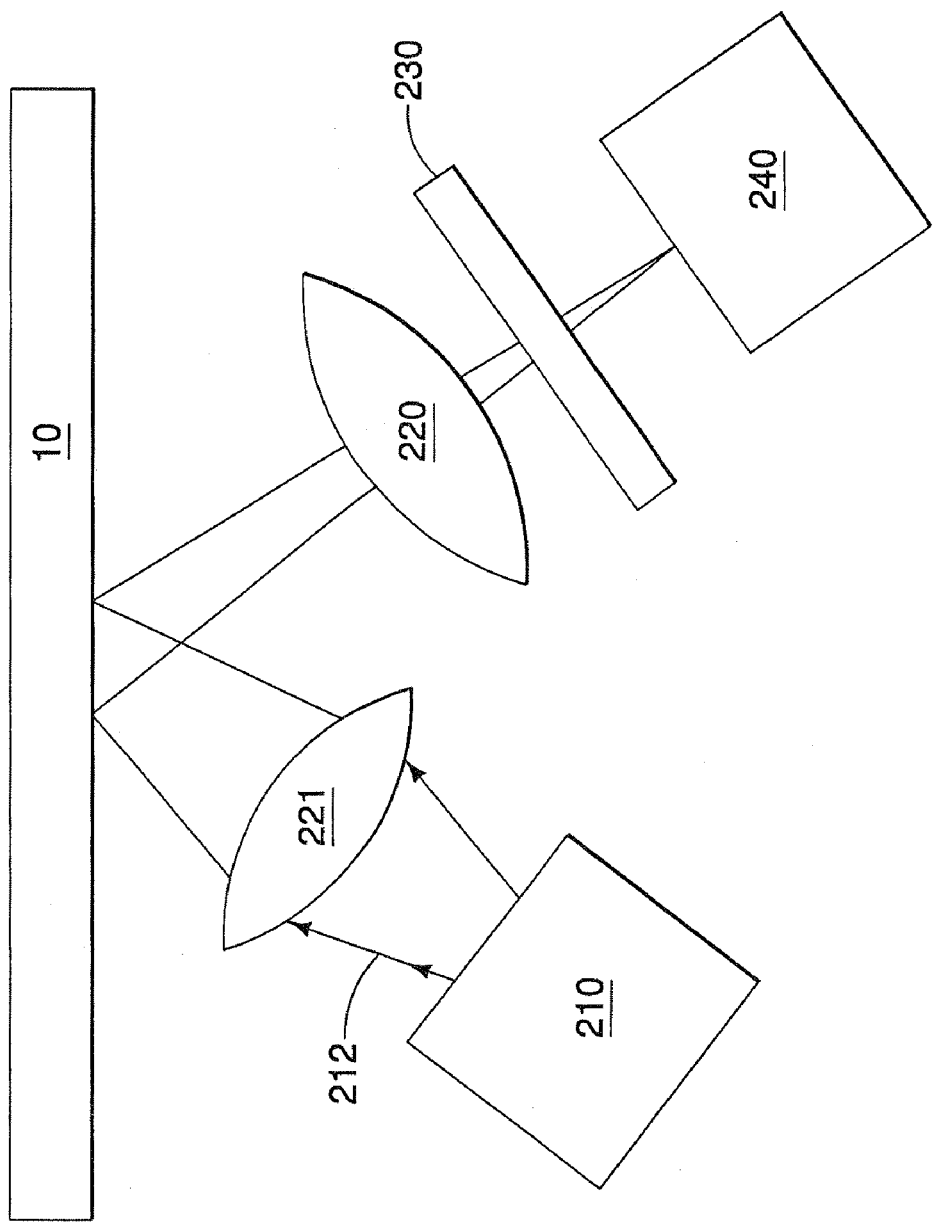
FIG. 10 is a schematic diagram of a device for analyzing a PCAT coating on a surface in accordance with certain embodiments of the invention.

FIG. 10 is a schematic diagram of a device for analyzing PCAT coatings on a surface in accordance with certain embodiments of the invention. In the example of FIG. 10, light source 210 may comprise an ultraviolet lamp, such as a deuterium lamp. Light energy 212 delivered by light source 210 may pass through a lens 221 prior to being reflected from a surface of substrate 10. Likewise, the reflected light energy may pass through lens 220 and filter 230 prior to being received by photodiode 240. Filter 230 may serve to reduce or block visible light from reaching photodiode 240, which could negatively affect the desired measurement.

Figure 11:
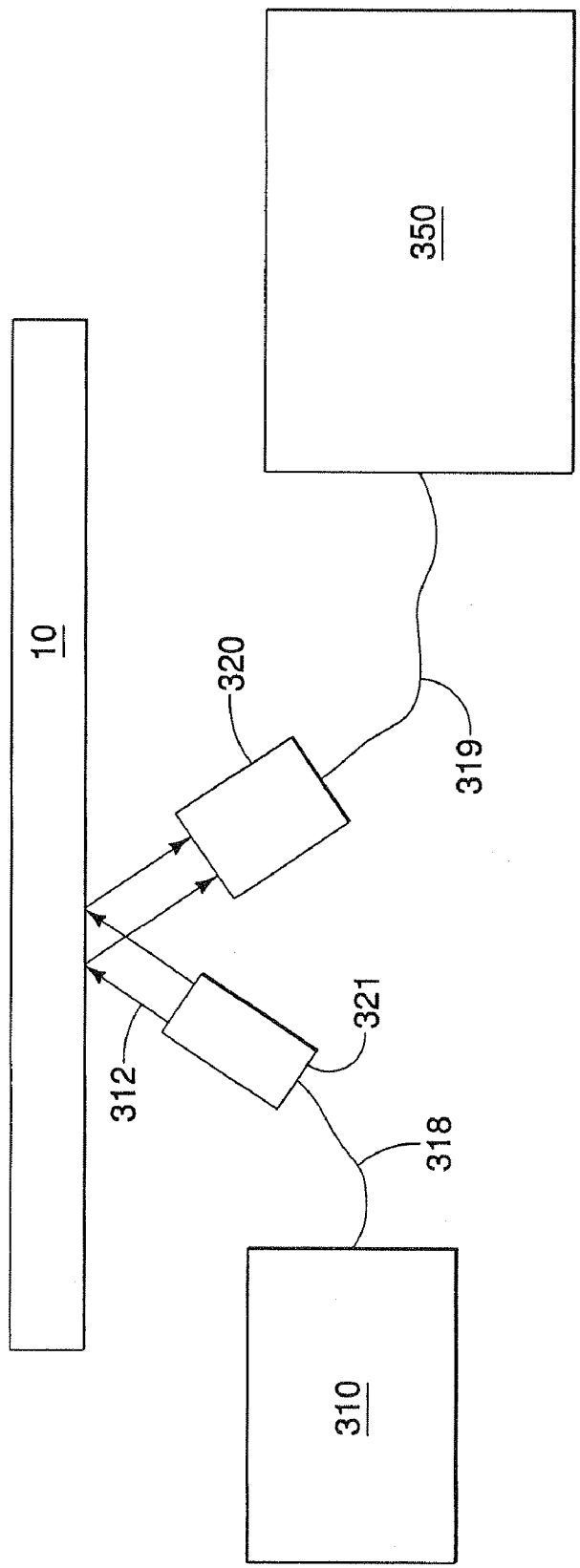
FIG. 11 is a schematic diagram of a device for analyzing a PCAT coating on a surface in accordance with certain embodiments of the invention.

FIG. 11 is a schematic diagram of a device for analyzing PCAT coatings on a surface in accordance with certain embodiments of the invention. In the embodiment shown in FIG. 11, light source 310 may comprise an ultraviolet lamp, such as a deuterium lamp. Light energy 312 is directed from light source 310 to a collimator/lens adapter 321 via an optical fiber 318. The collimator/lens adapter 321 directs light energy 312 to a surface of substrate 10. Reflected light energy is then received by a second collimator/lens adapter 320 and directed to a spectrophotometer 350 via an optical fiber 319. Spectrophotometer 350 may include software programs to interact with and manipulate the reflected light energy signal received by the spectrophotometer. Spectrophotometer 350 comprises a device that can measure light intensity as a function of the wavelength of the light received.

Figure 12:
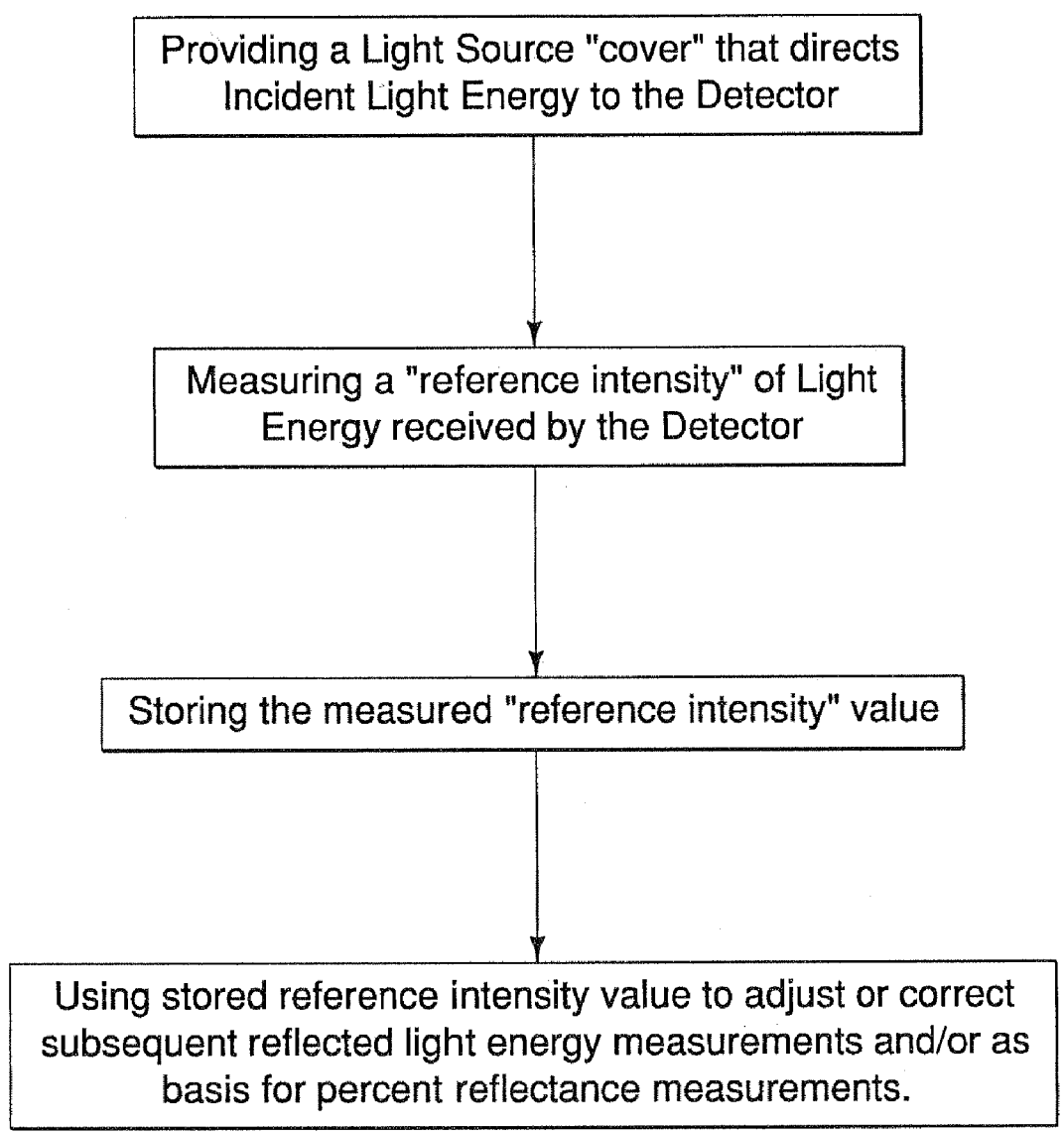
FIG. 12 is a block diagram of a method of calibrating a device for analyzing a PCAT coating on a surface in accordance with certain embodiments of the invention.

A device for analyzing PCAT coatings, such as the devices described with reference to FIGS. 9-11, may require calibration in order to produce reliable results. FIG. 12 is a block diagram of a method of calibrating a device for analyzing PCAT coatings on a surface in accordance with certain embodiments of the invention. The method shown in FIG. 12 may involve providing a light source "cover" or "conduit" to direct all incident light energy from the light source to the detector (i.e., the photodiode or spectrophotometer). Basically, the "cover" causes the equivalent of a 100% reflectance signal to be detected by the detector by ensuring that all light energy produced by the light source is received by the detector. The method may next include the step of measuring light energy received by the detector with the light source cover in place, defining this as the "calibration measurement." A next step in the method may include storing the measured value of light energy received by the detector in some type of storage medium. The method may next include a step of using the stored value of measured light energy to adjust or correct subsequent measurements. This last step may, for example, include providing a correction factor to subsequent measured values of reflected light energy received by the detector based upon the calibration measurement. Alternately, the calibration measurement may simply be stored to serve as a reference value (i.e., the denominator) for subsequent percent reflectance calculations. In one embodiment, for example, a measured value of reflected light energy from the surface of a substrate may be divided by the stored calibration measurement value to obtain a measure of percent reflectance.

Figure 13A:
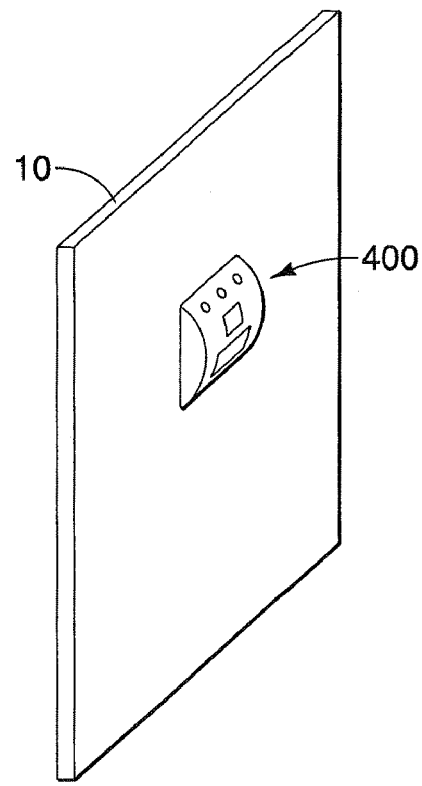
FIG. 13 is a perspective view of a portable device for analyzing a PCAT coating on a surface in accordance with certain embodiments of the invention.
Figure 13B:
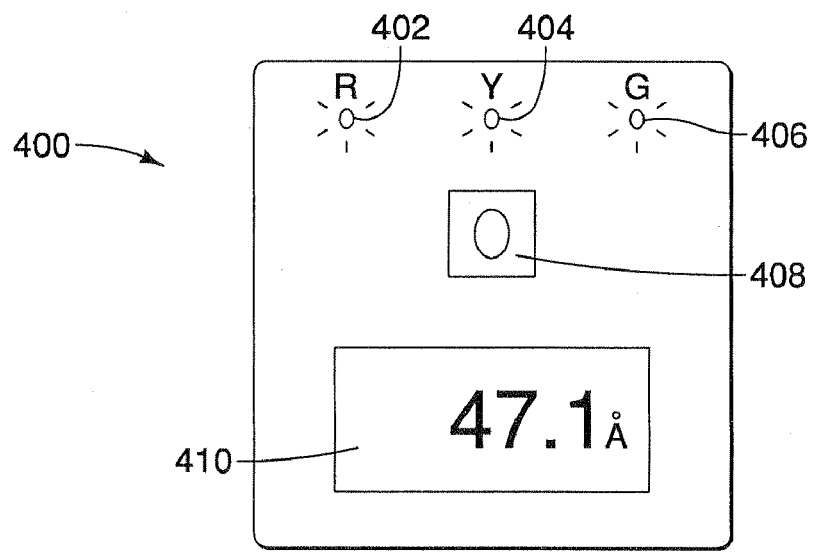

FIGS. 13 (a) and (b) show a portable device for analyzing PCAT coatings on a surface in accordance with certain embodiments of the invention. Portable device 400 is shown in FIG. 13 (a) in proximity to substrate 10 for analyzing for the presence of a PCAT coating thereon. In certain embodiments of the invention, portable device 400 may be placed in proximity to substrate 10 in a horizontal position (not shown), or in a vertical position as shown in FIG. 13 (a). This may allow flexibility in analyzing substrates, such as sheets of glass, regardless of the shipping or storage configuration, for example. In certain embodiments of the invention, the portable device 400 may be situated beneath a substrate 10 (i.e., a sheet of glass) adapted to pass over the portable device 400 such that a first surface 12 of the substrate may be analyzed for the presence of a PCAT coating thereon. In some embodiments, the portable device 400 may be adapted to analyze the presence of PCAT coatings on the surface of a substrate without being placed in contact with the surface.

FIG. 13 (b) is a front view of portable device 400. Portable device 400 may, for example, include a user-actuated button 408 to initiate a measurement. In certain embodiments of the invention, the actuation of button 408 and the subsequent analysis performed by the portable device 400, may result in the illumination of an LED, such as LEDs 402, 404, and 406. LEDs 402, 404, and 406 may convey useful information to a user, for example, by illuminating a green LED 406 to indicate the presence of a PCAT coating. Likewise, illuminating a red LED 402 may indicate the absence of a PCAT coating. A yellow LED 404 may also be employed, for example, to indicate that the measurement was not conclusive as to the presence or absence of a PCAT coating and that the analysis should be performed again. Other forms of conveying such information to a user based on a measured result (for example, audible tones, alphanumeric readouts or printouts, dials, gauges, etc) may be employed by those of ordinary skill in the art with the benefit of these teachings. Such minor modifications are contemplated and are deemed to fall within the scope of the invention. Also shown in the example of FIG. 13 (b) is a display screen 410 which may be used to display the measured thickness of a PCAT coating according to certain embodiments of the invention.

The detection system may also be used to determine the thickness of the PCAT coating. For example, with reference to FIG. 6, one knows that a PCAT coating 25 Angstrom thick should have a light reflectance of about 15% at a wavelength of 280 nm. If the reflectance curve shows that it is greater than 15% one knows that a thicker PCAT coating is present. If it is less than 15% one knows that a thinner PCAT coating is present. In addition, the data from graphs such as that shown in FIG. 6 may be stored so that a measured reflectance curve can be compared with that data and a thickness of the PCAT coating may be derived. Thus, for example, if a substrate having an unknown PCAT thickness is measured and a reflectance of about 18% at 280 nm is measured, then one knows that the PCAT thickness is about 30 Angstrom. Also, for quality assurance purposes, ranges may be set up that if the measured reflectance falls within a specified range, the thickness of the PCAT coating is right. If it falls outside the range, the thickness does not meet quality standards.

Thus, embodiments of a METHOD AND APPARATUS FOR IDENTIFYING THE PRESENCE OF THIN COATINGS are disclosed. One skilled in the art will appreciate that the invention can be practiced with embodiments other than those disclosed. The disclosed embodiments are presented for purposes of illustration and not limitation, and the invention is limited only by the claims that follow.

What is claimed is:

1. A method of determining whether a photocatalytic coating is present on the surface of a glass substrate, the method comprising:
    providing a source of light energy, at least a portion of the light energy having a wavelength below 350 nanometers (nm);
    directing light energy from the source toward the surface of the glass substrate;
    detecting light energy reflected from the surface of the glass substrate;
    measuring an intensity level of the reflected light energy at wavelengths below 350 nm; and
    determining whether a photocatalytic coating having a thickness of less than 200 angstroms is present on the surface of the glass substrate based on the measured intensity level of reflected light energy at wavelengths below 350 nm.

2. The method of claim 1 wherein the presence of a titanium-containing photocatalytic coating on the surface of the glass substrate is determined.

3. A device for determining whether a photocatalytic coating is present on a surface of a glass substrate comprising:
    a source of light energy having wavelengths below 350 nanometers (nm);
    means for directing the light energy from the source toward a surface of the glass substrate;
    detector means for detecting light energy reflected from the surface of the glass substrate;
    measuring means for measuring an intensity level of light energy reflected from the surface of the glass substrate; and
    processing means for determining whether a photocatalytic coating having a thickness of less than 200 angstroms is present on the surface of the glass substrate based on the measured intensity level of reflected light energy.

4. The device of claim 3 wherein the light energy comprises laser energy having wavelengths below 350 nm.

5. The device of claim 4 wherein the laser energy has wavelengths between 250 and 320 nm.

6. The device of claim 5 wherein the laser energy has a wavelength of 280 nm.

7. The device of claim 4 wherein the laser energy includes a range of wavelengths that spans less than 10 nm.

8. The device of claim 3 further comprising a filter adapted to allow reflected light energy within a specified range of wavelengths to pass through to the detector means.

9. The device of claim 8 wherein the specified range of wavelengths falls between 250 and 320 nm.

10. The device of claim 3 wherein the means for directing the light energy is adapted to direct the light energy toward the surface of the glass substrate at an angle of incidence between 0 and 89 degrees.

11. The device of claim 10 wherein the angle of incidence is between 1 and 45 degrees.

12. The device of claim 3 wherein the processing means is further adapted to calculate reflectance using the measured intensity of light energy reflected from the surface of the glass substrate.

13. The device of claim 12 wherein the processing means is further adapted to determine that a photocatalytic coating is present on the surface of the glass substrate when calculated reflectance is greater than a specified amount.

14. The device of claim 13 wherein the processing means is adapted to determine that a photocatalytic coating is present on the surface of the glass substrate when calculated reflectance is greater than 9%.

15. The device of claim 14 wherein the processing means is further adapted to determine that a photocatalytic coating is not present on the surface of the glass substrate when calculated reflectance is less than a specified amount.

16. The device of claim 3 wherein the light energy comprises an LED.

17. The device of claim 16 wherein the LED has a wavelength of 280 nm.

18. A method of determining whether a photocatalytic coating is present on the surface of a glass substrate, the method comprising:
    providing a source of light energy;
    directing electromagnetic energy from the source toward the surface of the glass substrate, wherein at least a portion of the electromagnetic energy comprises energy having wavelengths below 350 nanometers (nm);
    detecting electromagnetic energy reflected from the surface of the glass substrate;
    measuring an intensity level of the reflected electromagnetic energy; and
    determining whether a photocatalytic coating having a thickness of less than 200 angstroms is present on the surface of the glass substrate based on the measured intensity level of the reflected electromagnetic energy.

19. The method of claim 18 wherein the photocatalytic coating has a thickness of less than 100 angstroms.

20. A method of measuring the thickness of a photocatalytic coating on a surface of a glass substrate, the method comprising:
    providing a source of light energy, at least a portion of the light energy having a wavelength below 350 nanometers (nm);
    directing light energy from the source toward the surface of the glass substrate;
    detecting light energy reflected from the surface of the glass substrate;
    measuring an intensity level of the reflected light energy at wavelengths below 350 nm; and
    determining the thickness of a photocatalytic coating having a thickness of less than 200 angstroms on the surface of the glass substrate based on the measured intensity level of reflected light energy at wavelengths below 350 nm.

21. An apparatus for measuring the thickness of a photocatalytic coating on a glass substrate comprising:
    a source of light energy having wavelengths below 350 nanometers (nm);
    means for directing the light energy from the source toward a surface of the glass substrate;
    detector means for detecting light energy reflected from the surface of the glass substrate;
    measuring means for measuring an intensity level of light energy reflected from the surface of the glass substrate; and
    processing means for determining the thickness of a photocatalytic coating having a thickness of less than 200 angstroms on the surface of the glass substrate based on the measured intensity level of reflected light energy at wavelengths below 350 nm.

* * * * *